United States Patent [19]

Buchwald et al.

[11] Patent Number: 5,489,682
[45] Date of Patent: Feb. 6, 1996

[54] CATALYTIC ASYMMETRIC REDUCTION OF ENAMINES

[75] Inventors: Stephen L. Buchwald, Somerville; Nancy E. Lee, Brookline, both of Mass.

[73] Assignee: Massachusetts Institute of Technology, Cambridge, Mass.

[21] Appl. No.: 195,358

[22] Filed: Feb. 10, 1994

Related U.S. Application Data

[63] Continuation-in-part of Ser. No. 90,338, Jul. 12, 1993, Pat. No. 5,442,119, and a continuation-in-part of Ser. No. 792,229, Nov. 14, 1991, Pat. No. 5,292,893, and a continuation-in-part of Ser. No. 616,892, Nov. 21, 1990, Pat. No. 5,286,878.

[51] Int. Cl.$^6$ ............ C07D 207/02; C07D 207/06; C07D 307/02; C07C 209/40; C07C 209/52

[52] U.S. Cl. ............ 544/106; 548/530; 564/356; 564/357; 564/358

[58] Field of Search ............ 564/356, 357, 564/358; 544/106; 548/530

[56] References Cited

PUBLICATIONS

Cesarotti et al, Angew. Chem. Int. Ed. Engl., vol. 18, pp. 779 to 780 (1979).

Willoughby, C. A., et al., *J. Am. Chem. Soc.* 1992, 114, 7562.

Willoughby, C. A., et al., *J. Org. Chem.*, 1993, 58, 7627.

Broene, R. D., et al., *J. Am Chem. Soc.* 1993, 115, 12569.

Halterman, R. L., et al., *Organometallics*, 1988, 7, 883.

Halterman, R. L., et al., *J. Am. Chem. Soc.*, 1987, 109, 8105.

Takaya, H., et al., "Asymmetric Hydrogenation", Ch. 1 of *Catalytic Asymmetric Synthesis*, VCH Publishers, Inc., 1993 (Ojima, I., ed).

Ojima, Iwao, et al., *Tetrahedron*, 1989, 45, 6901.

*Primary Examiner*—Floyd D. Higel
*Attorney, Agent, or Firm*—Thomas J. Engellenner; William C. Geary, III; Lahive & Cockfield

[57] ABSTRACT

A catalytic asymmetric reduction process, which, by hydrogenating enamines, yields a corresponding amine having a high level of enantiomeric purity is disclosed. The reduction process utilizes a chiral metal catalyst that includes a metal or metal complex that is selected from groups 3, 4, 5, or 6, lanthanides and actinides. Moreover, the process uses hydrogen as the stoichiometric reducing agent and may be carried out at pressures ranging from about 0.5 to 200 atmospheres.

8 Claims, No Drawings

CATALYTIC ASYMMETRIC REDUCTION OF ENAMINES

GOVERNMENT SUPPORT

The U.S. Government has rights in this invention pursuant to NIH Grant Number GM 46059.

REFERENCE TO RELATED APPLICATIONS

This is a continuation-in-part of U.S. patent application Ser. Nos. 090,338, filed Jul. 12, 1993, now U.S. Pat. No. 5,442,719, entitled "Catalytic Asymmetric Reduction of Trisubstituted Olefins"; 792,229, filed Nov. 14, 1991, now U.S. Pat. No. 5,292,893, entitled "Catalytic Asymmetric Reduction of Imines and Oximes"; and 616,892, filed Nov. 21, 1990 now U.S. Pat. No. 5,286,878, entitled "Catalytic Reduction of Organic Carbonyls".

BACKGROUND OF THE INVENTION

The present invention relates to processes for the catalytic asymmetric reduction of enamines.

Processes that economically and efficiently produce enantiomerically enriched organic compounds are of great interest since these compounds are widely used as pharmaceuticals and specialty chemicals. More specifically, reactions that reduce enamines to yield enantiomerically enriched amine products are commercially quite significant as they can be used in the large scale preparation of pharmaceuticals and specialty chemicals. Thus, the effectiveness and economy of such reduction reactions are important considerations.

Currently, there are no known methods of producing enantiomerically enriched products by hydrogenation of those enamines that are 1,1-disubstituted olefins. Such methods would be useful in many synthesis reactions to provide enantiomerically enriched amines.

Accordingly, it would be advantageous to provide an economical and efficient processes for asymmetrically reducing certain enamines.

It is thus an object of the invention to provide economical and effective processes for the asymmetric reduction of enamines that are 1,1-disubstituted olefins. Another object is to provide effective processes to obtain from such enamines enantiomerically enriched amines. Other objects will be apparent upon reading the disclosure that follows.

SUMMARY OF THE INVENTION

The disclosures of the related parent applications, U.S. patent application Ser. Nos. 090,338, filed Jul. 12, 1993 entitled "Catalytic Asymmetric Reduction of Trisubstituted Olefins; 792,229, filed Nov. 14, 1991 entitled Catalytic Asymmetric Reduction of Imines and Oximes"; and 616,892, filed Nov. 21, 1990, entitled "Catalytic Reduction of Organic Carbonyls", are all hereby incorporated by reference.

Unless otherwise clear from its context, the term "catalyst" is used interchangeably herein to refer both to the metal complexes or precatalysts before their activation as catalytic species, and to the active catalytic species themselves.

The invention provides an effective process for the catalytic asymmetric reduction of those enamines which are 1,1-disubstituted olefins to yield chiral amines enriched in one enantiomer. Hereinafter the term "enamine" is used to refer to those enamines that are 1,1-disubstituted olefins.

Such enamines contain a carbon-carbon double bond with one substituent that is an alkyl group (saturated or unsaturated), an aryl group, a heteroaromatic group, or a substituted version thereof. The other substituent on the same carbon is either a mono- or di-substituted amino group. Such enamine molecules are represented by the general structural formula:

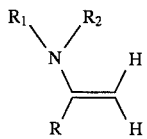

Generally, the process of the invention involves first generating an active species of an effective, optically active reduction catalyst which is used in the reaction. The substrate is then reacted with the active catalyst at a temperature range of 0° C. to 100° C. and at pressures ranging from 0.5 to 200 atmospheres of hydrogen. When the reaction is complete one need only perform conventional separation and purification techniques to yield the desired enantiomerically enriched end product.

Formation of the active catalyst can be effected by dissolving the precatalyst in an organic solvent in an inert atmosphere or in an atmosphere of hydrogen. Thereafter, the precatalyst/solvent mixture can be subjected to between 1 and 2 equivalents, relative to the amount of precatalyst, of an alkylating or reducing agent. The reaction mixture can then be placed in an atmosphere of hydrogen gas at a pressure between 0.5 and 200 atmospheres. The reaction can then be conducted using hydrogen alone, or in combination with a substoichiometric amount of a silane relative to the amount of substrate.

The process of the invention preferably is carried out where hydrogen serves as the reducing agent. In such an embodiment the active catalytic species is generated under an inert gas such as argon or nitrogen, or under an atmosphere of hydrogen. Thereafter, a substoichiometric quantity of a silane compound (relative to the substrate) may optionally be added. The reduction reaction takes place in an atmosphere of hydrogen which is present in excess and serves as the stoichiometric reductant.

In another embodiment no alkylation is necessary. The reaction is able to proceed by mixing together, in a hydrogen atmosphere, in a suitable reaction vessel, the precatalyst, the desired substrate, and, optionally, a substoichiometric quantity, relative to substrate, of a silane compound.

The reduction of enamines by this reaction yields, after quenching of the catalyst, a crude end product in a more reduced form than the starting compound. The end product may then be purified by known techniques.

DETAILED DESCRIPTION OF THE INVENTION

The process of the invention can be used to effect the catalytic asymmetric reduction of enamines that are 1,1-disubstituted olefins to produce amines that are enriched in one enantiomer. The catalyst used in the reduction reaction preferably is enriched in one enantiomer. Generally, an enantiomerically enriched catalyst is one which has more than 50 percent of one enantiomer. More specifically, an enantiomerically enriched catalyst is one which has greater than 80%, and most preferably greater than 90% of one enantiomer.

The enamine substrates to which the invention is directed are represented by the formula shown below:

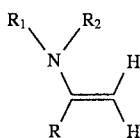

where R is an alkyl group (saturated or unsaturated), an aryl group, a heteroaromatic group, or a substituted version thereof, and where $R_1$ and $R_2$ are alkyl groups (saturated or unsaturated), aryl groups, heteroaromatic groups, or substituted versions thereof, or hydrogen, except that $R_1$ and/or $R_2$ are not of the formula $C(O)R_3$. Further, $R_1$ and $R_2$ may be part of a ring system; or R and $R_1$ may be part of a ring system; or R and $R_2$ may be part of a ring system.

The enamine substrates that are useful with the processes of the present invention are converted to amines in a more reduced state that have the general formula $((R_1)NR_2)(R)(H)CCH_3$, where R is an alkyl group (saturated or unsaturated), an aryl group, a heteroaromatic group, or a substituted version thereof, and where R is not H or D. Further, $R_1$ and $R_2$ are alkyl groups (saturated or unsaturated), aryl groups, heteroaromatic groups, or a substituted version thereof. $R_1$ and $R_2$ can also be hydrogen, but $R_1$ and/or $R_2$ are not of the formula $C(O)R_3$. $R_1$ and $R_2$ further may be part of a ring system; or $R_1$ and R may be part of a ring system; or $R_2$ and R may be part of a ring system.

The basic steps of the invention involve first generating an active species of an effective, optically active catalyst. This can be accomplished by dispensing a suitable optically active precatalyst in an organic solvent such as tetrahydrofuran, ether, toluene, benzene, hexane, or the like. Preferably, this mixture is maintained in an atmosphere of an inert gas, such as argon or nitrogen, or in an atmosphere of hydrogen gas. In some instances, especially where certain titanium-containing catalysts are used, as explained below in more detail, the precatalyst may be activated by dissolving the catalyst in a solvent, followed by the addition of an alkylating agent. Thereafter, a substoichiometric quantity of a silane compound, relative to the substrate, may optionally be added to the reaction mixture. The desired substrate is added to the mixture and the reactants may be transferred to a reaction vessel that is able to be charged with hydrogen at ambient or elevated pressures.

The reduction reactions of the present invention preferably use hydrogen as the stoichiometric reducing agent. The hydrogen reducing agent can be used alone, or it can be used in combination with a substoichiometric amount, relative to the substrate, of a silane compound.

Where the reaction is to be conducted using hydrogen as the reducing agent at high pressure, the precatalyst/solvent mixture is, optionally, subjected to vacuum to remove the inert gas, and hydrogen gas can then be added to the reactor vessel. The reactor vessel contents can then be cooled to about 0° C. and allowed to equilibrate. Thereafter, an alkylating agent is generally added to the reactor vessel. Optionally, a silane compound can then be added at a substoichiometric amount relative to the substrate. The desired substrate is then added and the reaction vessel can be sealed and placed in a dry box. The vessel is then transferred to a high pressure reactor (such as a Parr® high pressure reactor) and it is removed from the dry box. The reactor is then charged with hydrogen at a desired pressure and the reaction commences upon heating to between 25°–100° C. The reaction can be conducted in hydrogen at a pressure ranging from 0.5 atmosphere to over 200 atmospheres.

The reaction typically requires from 1 to 200 hours to complete. Once completed, the reaction vessel is cooled to room temperature, vented and opened to air to quench the catalyst. Well known separation and purification techniques can then be utilized to obtain the end product, which is enriched in one enantiomer.

One of ordinary skill in the art will appreciate that minor modifications may be made to the reduction reaction without exceeding the scope of the invention. To some extent the Examples presented herein illustrate alternative techniques for conducting reduction reactions according to the invention.

The present reduction reaction preferably requires between about 0.1–40% by mole of catalyst relative to the substrate, and more preferably, between about 5–10% by mole of catalyst relative to the substrate.

A variety of precatalysts can be used effectively in the reduction reactions of the present invention. Exemplary precatalysts broadly include those that are chiral, either by virtue of the chirality of a ligand or by virtue of chirality at the metal center. Exemplary precatalysts are chiral precatalysts having the general formulas:

$$M(L)(L')(L'') \qquad (1)$$

$$M(L)(L')(L'')(L''') \qquad (2)$$

$$M(L)(L')(L'')(L''')(L^{iv}) \qquad (3)$$

$$M(L)(L')(L'')(L''')(L^{iv})(L^{v}) \qquad (4)$$

where M is a group 3, 4, 5 or 6 metal, a lanthanide, or an actinide and where L, L', L'', and L''', $L^{iv}$ and $L^{v}$, independently, can be some combination of H, an alkyl group, an aryl group, a cyclopentadienyl group, Si(R)(R')(R''), a halogen, -OR, -SR, -NR(R'), or PR(R')(R''), where R, R' and R'' may be H, an alkyl, aryl, or silyl group and may be different or the same. A cyclopentadienyl group (designated "Cp") is represented by the formula

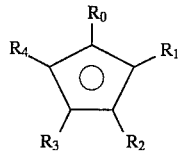

where $R_0$, $R_1$, $R_2$, $R_3$, and $R_4$ may be hydrogen, alkyl, aryl, Si(R)(R')(R''), a halogen, -OR, -SR, -NR(R'), PR(R')(R''), or -PR(R'), where R, R' and R'' may be H, an alkyl, aryl, or silyl group and may be different or the same. Examples of group 3, 4, 5 or 6 metals which may be useful with the present invention include titanium, vanadium, niobium, and chromium. Examples of useful lanthanides include yttrium, scandium, lanthanium, samarium, ytterbium, and lutetium. Examples of useful actinides include thorium and uranium. Titanium, however, is the most preferred metal.

A preferred precatalyst, which is particularly useful in conducting catalytic asymmetric reduction reactions is generally represented by the formula $$Y_2MX_n$$

where Y represents a substituted cyclopentadienyl or indenyl group or where $Y_2$ represents a substituted bis-cyclopentadienyl or bis-indenyl group; M represents a group 3, 4, 5, 6 metal, a lanthanide or an actinide; X represents groups including halides, alkoxides, amides, sulfides, phosphines, alkyls, aryls, hydrides, and mono-, di-, and tri-substituted silyls, and carbon monoxide; and $X_2$ can be an $\eta^2$-olefin or an $\eta^2$-alkyne; and n is an integer from 1 to 4. In a preferred embodiment $Y_2$ is ethylene-1,2-bis($\eta^5$-4,5,6,7-tetrahydro- 1-indenyl) and X₂ represents 1,1'-binaphth-2,2'-diolate.

Precatalysts having the ethylene-1,2-bis(η⁵-4,5,6,7-tetrahydro-1-indenyl backbone are referred to herein as "BIE" catalysts. Specific preferred catalysts for asymmetric reduction include (R,R)-ethylene-1,2-bis (η⁵-4,5,6,7-tetrahydro-1-indenyl)titanium-(R)- 1,1'-binaphth-2,2'-diolate; (S,S)-ethylene-1,2-bis(η⁵-4,5,6,7-tetrahydro-1-indenyl) titanium-(S)-1,1'-binaphth-2,2'-diolate; (R,R)-1,1'-Trimethylenebis(η⁵-3-tertbutylcyclopentadienyl) -titanium(IV) dichloride; (S,S)-1,1'-Trimethylenebis(η⁵-3-tertbutylcyclopentadienyl) -titanium(IV) dichloride; (R,R)-Ethylene-bis(η⁵-4,5,6,7-tetrahydro -1-indenyl)titanium(IV) dichloride; (S,S)-Ethylene-bis(η⁵-4,5,6,7-tetrahydro-1indenyl)titanium(IV) dichloride;.(R,R)-2,2'-bis(1-indenylmethyl)1-(1'-binaphthyl titanium(IV) dichloride; (S,S)-2,2'-Bis(1-indenylmethyl)1-1'-binaphthyl titanium(IV) dichloride; (R,R)-Ethylene-bis(η⁵-4,5,6,7-tetrahydro-1-indenyl) dimethyl titanium(IV); and (S,S)-Ethylene-bis(η⁵-4,5,6,7-tetrahydro-1-indenyl) dimethyl titanium(IV).

The BIE-type precatalysts useful with the catalytic asymmetric reduction reactions of the invention are enriched in one enantiomer of the molecule. Enantiomeric enrichment, as the term is used herein, requires more than 50% of and enantiomer, and more preferably requires more than 80% of one enantiomer. In a preferred embodiment, an enantiomerically enriched catalyst has more than 90% of one enantiomer.

Other preferred catalysts include metal alkoxides and metal aryloxides such as titanium alkoxides and titanium (IV) aryloxides. Specific examples of such catalysts include (R,R)-2,2'-Dimethyl-α,α,α',α'-tetrakis(β-napthyl)-1,3-dioxolan-4,5-dimethoxy diisopropoxy titanium(IV) and (S,S)-2, 2'-Dimethyl-α,α,α', α'-tetrakis(β-napthyl)-1,3-dioxolan-4, 5-dimethoxy diisopropoxy titanium(IV).

Precatalysts, including BIE catalysts, may need to be activated by reaction with an alkylating agent or reducing agent, preferably in an organic solvent. Suitable alkylating agents are known to those skilled in the art and generally include organometallic compounds. Examples of such compounds include alkylmagnesium halides, alkyllithium compounds, alkyl aluminum compounds and boron, aluminum, or other metal alkyls or metal hydrides. Particularly preferred alkylating agents include n-pentylnagnesium bromide and n-butyllithium. Preferred reducing agents include sodium bis(2-methoxyethoxy) aluminum hydride (Red Al®). Preferably, about 100 to 200% by mole of the alkylating agent (relative to precatalyst) should be reacted with the precatalyst in order for activation to occur. The activation of such catalysts by reaction with an alkylating agent is further described and illustrated in the examples.

Metal alkoxide and metal aryloxide catalysts may be air stable, and may be self-activating (i.e., require no alkylation step), or may be activated by the presence of a silane compound.

The catalysts useful in this invention may be active as electronically neutral molecules, anions or cations.

One skilled in the art will appreciate that a variety of solvents may be used with these catalysts. One general requirement of a suitable solvent is that the catalyst must be completely or partially soluble within the solvent. Complete solubility is not required as there need only be enough catalyst present in the solution to facilitate a reaction. Exemplary solvents include tetrahydrofuran, toluene, benzene, hexane, ether and the like.

As noted above, hydrogen is the reducing reagent used in the present catalytic asymmetric reduction processes. Hydrogen may be used alone or in the presence of a substoichiometric amount (relative to the substrate) of a silane compound. A suitable silane compound is one that possesses a silicon-hydrogen bond. Exemplary silane compounds which may be used in these processes (with a hydrogen reducing agent) are represented by the formulas shown below.

   (5)

   (6)

   (7)

   (8)

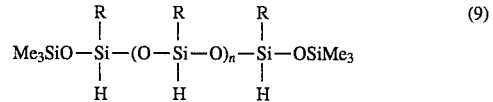   (9)

where R, R' and R" represent alkyl, aryl or hydride groups and may be the same or different. Specific examples of suitable silane reducing reagents include silane, diphenylsilane, phenylsilane, diethylsilane, dimethylsilane, triethoxysilane, trimethoxysilane, and poly(methylhydrosiloxane).

The silane compound, when used in a substoichiometric amount, can be present at about 0.1 to 5 equivalents, and more preferably 0.1–2.5 equivalents, relative to the catalyst.

One aspect of the invention, as noted above, involves the catalytic asymmetric reduction of enamines to yield amines having a high degree of enantiomeric purity. The desired enamine substrate can be reduced to yield a product enriched in one enantiomer, using a suitable catalyst of the type described above, which is enriched in one enantiomer. A preferred catalyst is one which is enriched in (R,R)-ethylene-1,2-bis(η⁵-4,5,6,7-tetrahydro-1-indenyl) titanium-(R)-1,1'-binaphth-2,2'-diolate. Another preferred catalyst is one which is enriched in (S,S)-ethylene-1,2-bis (η⁵-4,5,6,7-tetrahydro-1-indenyl)titanium-(S)-1,1-binaphth -2,2'-diolate. Preferably, these catalysts contain at least about 80% of the (R, R, R) or (S,S,S) enantiomers, respectively.

The degree of enantiomeric excess ("ee") for the reaction product depends on a number of factors including the enantiomeric purity of the catalyst, the specific enamine substrate being reduced, and the reaction conditions. Many reactions conducted according to the process of the present invention yield end products having relatively high enantiomeric excesses. In some instances, the ee exceeds 90%.

The asymmetric reduction of enamine substrates is further described and illustrated by the examples that follow.

EXAMPLES

In the examples that follow all reactions were conducted under an atmosphere of argon or hydrogen using standard Schlenk techniques. Hydrogenation reactions were conducted in a Schlenk flask or in a Fisher-Porter bottle (purchased from Aerosol Lab Equipment, Walton, NY 13856). The enantiomeric excess values of the products were determined by analysis of ¹H NMR spectra of diastereomeric salts resulting from addition of (R) or (S) acetyl mandelic acid to the amines.

EXAMPLE 1:Reduction of 1-(1-pyrrolidinyl)-1-phenylethene to (R)-1-(1-pyrrolidinyl)- 1-phenylethane.

In a dry sealable Schlenk flask (300 mL) under a hydrogen atmosphere, (S,S)-ethylene- 1,2-bis(η⁵-4,5,6,7-tetrahydro-1-indenyl)titanium (S)-1,1'-binaphth-2,2' -diolate (35 mg, 0.058 mmol) was dissolved in THF (4 mL). A solution of n-butyllithium (0.065 mL, 1.7M in hexanes, 0.11 mmol, 1.91 equiv.) was added at which point the reaction turned from a dark red color to a green color. Phenylsilane (0.02 mL, 0.162 mmol, 2.7 equiv.) was added followed by a solution of 1-(1-pyrrolidinyl)-1-phenylethene (200 mg, 1.16 mmol, 20 equiv.) in THF (1 mL). The flask was sealed and the reaction mixture was stirred for 20 h at room temperature. The reaction was opened to air and the solvent was removed using a rotary evaporator. The crude residue was purified by chromatography on silica gel using methanol in methylene chloride (2.5% methanol in methylene chloride increased to 10%) to give, after concentration in vacuo, (R)-1-( 1-pyrrolidinyl)-1-phenylethane ( 159 mg, 0.91 mmol, 78%). The amine had an ee of 94%.

EXAMPLE 2: Reduction of 1-(1-pyrrolidinyl)-1-phenylethene to (S)-1-(1-pyrrolidinyl)-1-phenylethane.

In a dry sealable Schlenk flask (300 mL) under a hydrogen atmosphere, (R,R)-ethylene- 1,2-bis($\eta^5$-4,5,6,7-tetrahydro-1 -indenyl)titanium (R)-1,1 '-binaphth-2,2-diolate (35 mg, 0.058 mmol) was dissolved in THF (4 mL). A solution of n-butyllithium (0.065 mL, 1.7M in hexanes, 0.11 mmol, 1.91 equiv.) was added at which point the reaction turned from a dark red color to a green color. Phenylsilane (0.02 mL, 0.162 mmol, 2.7 equiv.) was added followed by a solution of 1-( 1-pyrrolidinyl)-1-phenylethene (200 mg, 1.25 mmol, 21 equiv.) in THF (1 mL). The flask was sealed and the reaction mixture was stirred for 44 h at room temperature. The reaction was opened to air and the solvent was removed using a rotary evaporator. The crude residue was purified by chromatography on silica gel using methanol in methylene chloride (2.5% methanol in methylene chloride increased to 10%) to give, after concentration in vacuo, (S)-1-( 1-pyrrolidinyl)-1-phenylethane (125 mg, 0.71 mmol, 57%). The amine had an ee of 94%.

EXAMPLE 3: Reduction of 1-(1-pyrrolidinyl)-1-(2'-naphthyl) ethene to 1-(1-pyrrolidinyl)- 1-(2'-naphthyl) ethane.

In a dry sealable Schlenk flask (300 mL) under a hydrogen atmosphere, (S,S)-ethylene- 1,2-bis($\eta^5$-4,5,6,7-tetrahydro-1-indenyl)titanium (S)-1,1'-binaphth-2,2'-diolate (35 mg, 0.058 mmol) was dissolved in THF (4 mL). A solution of n-butyllithium (0.065 mL, 1.7M in hexanes, 0.11 mmol, 1.91 equiv.) was added at which point the reaction turned from a dark red color to a green color. Phenylsilane (0.02 mL, 0.162 mmol, 2.7 equiv.) was added followed by a solution of 1-(1-pyrrolidinyl)-1-(2'-naphthyl ethene (200 mg, 0.98 mmol, 17 equiv.) in THF (1 mL). The flask was sealed and the reaction mixture was stirred for 24 h at room temperature. The reaction was opened to air and the solvent was removed using a rotary evaporator. The crude residue was purified by chromatography on silica gel using methanol in methylene chloride (2.5% methanol in methylene chloride increased to 10%) to give, after concentration in vacuo, 1-(1-pyrrolidinyl)-1-(2'-naphthyl) ethane (172 mg, 0.76 mmol, 78%). The amine had an ee of 95%.

EXAMPLE 4: Reduction of 1-pyrrolidinyl)1-(2'-methylphenyl) ethene to 1-1-pyrrolidinyl)- 1-(2-methylphenyl) ethane.

A dry Fisher-Porter bottle properly fitted with a complete with a gas inlet, pressure gauge, inlet valve and pressure release valve was charged with (S,S)-ethylene-1,2-bis($\eta^5$-4, 5,6,7-tetrahydro-1-indenyl)titanium (S)-1,1'-binaphth-2,2' -diolate (35 mg, 0.058 mmol). The system was evacuated and filled with hydrogen (5–10 psig). THF (4 mL) was added and the hydrogen pressure was increased to 80 psig. With a needle the bottle was vented until the hydrogen pressure was reduced back to 5–10 psig. A solution of n-butyllithium (0.065 mL, 1.7M in hexanes, 0.11 mmol, 1.91 equiv.) was added at which point the reaction turned from a dark red color to a green color. Phenylsilane (0.02 mL, 0.162 mmol, 2.7 equiv.) was added and the hydrogen pressure was increased to 80 psig. Using a high pressure syringe, a solution of 1-(1-pyrrolidinyl)-1-(2-methylphenyl) ethene (200 mg, 1.18 mmol, 20 equiv.) in THF (1 mL) was added. The reaction mixture was sealed and placed in an oil bath at 65° C. for 24 h. The reaction was cooled to room temperature and opened to air. The solvent was removed using a rotary evaporator and the crude residue was purified by chromatography on silica gel using methanol in methylene chloride (2.5% methanol in methylene chloride increased to 10%) to give, after concentration in vacuo, 1-(1-pyrrolidinyl)-1-(2-methylphenyl) ethane (189 mg, 1.01 mmol, 86%). The amine had an ee of 96%.

EXAMPLE 5: Reduction of 1-(4-morpholinyl)-1-(4-methoxyphenyl) ethene to 1-(4-morpholinyl)- 1-(4-methoxyphenyl) ethane.

A dry Fisher-Porter bottle properly fitted with a pressure coupling closure complete with a gas inlet, pressure gauge, inlet valve and pressure release valve was charged with (S,S)-ethylene-1,2-bis($\eta^5$-4,5,6,7-tetrahydro-1-indenyl)titanium (S)-1,1'-binaphth- 2,2'-diolate (35 mg, 0.058 mmol). The system was evacuated and filled with hydrogen (5–10 psig). THF (4 mL) was added and the hydrogen pressure was increased to 80 psig. With a needle the bottle was vented until the hydrogen pressure was reduced back to 5–10 psig. A solution of n-butyllithium (0.065 mL, 1.7M in hexanes, 0.11 mmol, 1.91 equiv.) was added at which point the reaction turned from a dark red color to a green color. Phenylsilane (0.02 mL, 0.162 mmol, 2.7 equiv.) was added and the hydrogen pressure was increased to 80 psig. Using a high pressure syringe, a solution of 1-(4-morpholinyl)-1-(4-methoxyphenyl) ethene (220 mg, 1.00 mmol, 17 equiv.) in THF ( 1 mL) was added. The reaction mixture was sealed and placed in an oil bath at 65° C. for 23 h. The reaction was cooled to room temperature and opened to air. The solvent was removed using a rotary evaporator and the crude residue was purified by chromatography on silica gel using methanol in methylene chloride (2.5% methanol in methylene chloride increased to 10%) to give, after concentration in vacuo, 1-(4-morpholinyl)-l-(4-methoxyphenyl) ethane (185 mg, 0.84 mmol, 84%). The amine had an ee of 91%.

The above examples are intended to be illustrative of the invention and should not be read to limit the invention to the specific reduction reactions provided in the examples. One skilled in the art will readily appreciate that the invention is applicable to a variety of reduction reactions in which the substrate is an enamine, and that a variety of catalysts may be used in these reduction reactions.

What is claimed is:

1. A catalytic asymmetric reduction process, comprising the steps of:

providing a catalytic amount of an active species of an enantiomerically enriched chiral catalyst selected from the group consisting of M(L)(L')(L"), M(L)(L')(L")(L'''), M(L)(L')(L")(L''')(L$^{iv}$), and M(L)(L')(L")(L''')(L$^{iv}$)(L$^v$), where M is a group 3, 4, 5 or 6 metal, a lanthanide or an actinide, and L, L', L", L''', L$^{iv}$, L$^v$, independently, is any combination of H, alkyl, aryl, Si(R)(R')(R"), halogen, -OR, SR, or -NR(R'), PR(R')(R"), or a cyclopentadienyl group having the formula

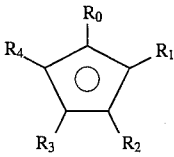

where R, R', and R" are H, alkyl, aryl, or silyl and are the same or different, and where $R_0$, $R_1$, $R_2$, $R_3$, and $R_4$ are hydrogen, alkyl, aryl, Si(R)(R')(R"), halogen, -OR, -SR,-NR(R'), PR(R')(R"), or -PR(R') groups in any combination, where R, R', and R" are as defined above:

reacting an enamine substrate in the presence of hydrogen and the catalyst, the enamine substrate having the formula:

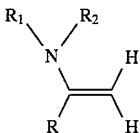

where R is an alkyl group (saturated or unsaturated), an aryl group, a heteroaromatic group, or a substituted version thereof, and $R_1$ and $R_2$ are hydrogen, alkyl groups (saturated or unsaturated), aryl groups, heteroaromatic groups, except that $R_1$ or $R_2$, or both $R_1$ and $R_2$, are not of the formula $C(O)R_3$; and recovering and purifying an the reduced enamine reaction product having a high level of enantiomeric purity.

2. The process of claim 1 wherein the step of reacting the enamine substrate in the presence of hydrogen as the reducing agent and the catalyst is conducted at a hydrogen pressure in the range of 0.5 atmosphere to 200 atmospheres.

3. The process of claim 2 wherein before the step of reacting the enamine substrate in the presence of hydrogen and the catalyst, a silane compound is added at a substoichiometric amount relative to the substrate.

4. The process of claim 1 wherein the enantiomerically enriched chiral catalyst is a titanium-containing catalyst selected from the group consisting of L(L')(L")Ti; L(L')(L")(L''')Ti; L(L')Ti-X; L(L')(L")Ti-X; L(L')Ti-X$_2$; L(L')Ti-H; and L(L')(L")TiH where X is a halogen, and where L, L', L" and L''', independently, is any combination of H, alkyl, aryl, Si(R)(R')(R"), halogen,-OR,-SR, or -NR(R'),-PR(R')(R"),or a cyclopentadienyl group of the structure

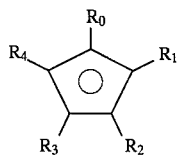

where R, R', and R" are H, alkyl, aryl, or silyl and are the same or different, and where $R_0$, $R_1$, $R_2$, $R_3$, and $R_4$ are hydrogen, alkyl, aryl, Si(R)(R')(R"), halogen. -OR, -SR,-NR(R'), -PR(R')(R"), or-PR(R') groups in any combination, where R, R', and R" are as defined above.

5. The process of claim 4 wherein the catalyst is an enantiomerically enriched chiral complex selected from the group consisting of chiral bis(cyclopentadienyl) titanium monohalide complexes; chiral bis(cyclopentadienyl) titanium monoalkoxide complexes; chiral bis(cyclopentadienyl) titanium dihalide complexes; chiral bis(cyclopentadienyl) titanium dialkoxide complexes; and chiral bis(cyclopentadienyl) titanium diaryloxide complexes.

6. The process of claim 5 wherein the catalyst is selected from the group consisting of (R,R)-ethylene-1,2-bis($\eta^5$-4, 5, 6, 7-tetrahydro-1-indenyl) titanium-(R)-1,1-binapth- 2,2'-diolate and (S,S)-ethylene-1,2-bis($\eta^5$-4, 5, 6, 7-tetrahydro-1-indenyl) titanium-(S)-1,1-binapth-2,2'-diolate.

7. The process of claim 1 wherein the catalyst is present at about 0.1 to 10% by mole, relative to the substrate.

8. The process of claim 7 wherein the reaction is conducted at a temperature ranging from about 0° to 100° C.

* * * * *